United States Patent [19]

Richardson et al.

[11] 4,350,044
[45] Sep. 21, 1982

[54] METHOD OF AND APPARATUS FOR TESTING WOODEN POLES

[75] Inventors: Roy Richardson, Leeds; Bernard Czenkusz, Bradford, both of England

[73] Assignee: Yorkshire Electricity Board, Leeds, England

[21] Appl. No.: 217,330

[22] Filed: Dec. 17, 1980

[30] Foreign Application Priority Data

Dec. 19, 1979 [GB] United Kingdom ............... 7943725

[51] Int. Cl.³ ............................................. G01N 29/04
[52] U.S. Cl. .................................... 73/600; 73/632
[58] Field of Search ............. 73/579, 584, 589, 599, 73/600, 624, 632

[56] References Cited

U.S. PATENT DOCUMENTS

| | | | |
|---|---|---|---|
| 3,066,525 | 12/1962 | Harris | 73/627 |
| 3,190,111 | 6/1965 | Trussell et al. | 73/600 |
| 3,345,861 | 10/1967 | Heath | 73/579 |
| 3,521,483 | 7/1970 | Miller et al. | 73/598 |
| 3,531,983 | 10/1970 | Heath et al. | 73/584 |
| 3,600,937 | 8/1971 | Nilberg | 73/598 |
| 3,877,294 | 4/1975 | Shaw | 73/584 |
| 4,059,988 | 11/1977 | Shaw | 73/579 |
| 4,074,564 | 2/1978 | Anderson | 73/609 |

*Primary Examiner*—James J. Gill
*Attorney, Agent, or Firm*—Beveridge, DeGrandi & Kline

[57] ABSTRACT

For testing wooden poles, a transmitter unit including a piezo electric transducer, energized to produce repetitive pulses of ultrasonic frequency, is held against the pole. The transmitter unit produces an audible sound synchronously with each ultrasonic pulse. A portable receiver unit having a probe coupled to a piezo electric transducer is held against the pole. This receiver unit includes a signal level comparator which causes a lamp to flash on for each received ultrasonic pulse above a predetermined amplitude. The receiver is held in a plurality of positions and readings are noted where the lamp flashes synchronously with the audible signal. From these readings the strength remaining in the pole to resist bending forces is calculated.

13 Claims, 8 Drawing Figures

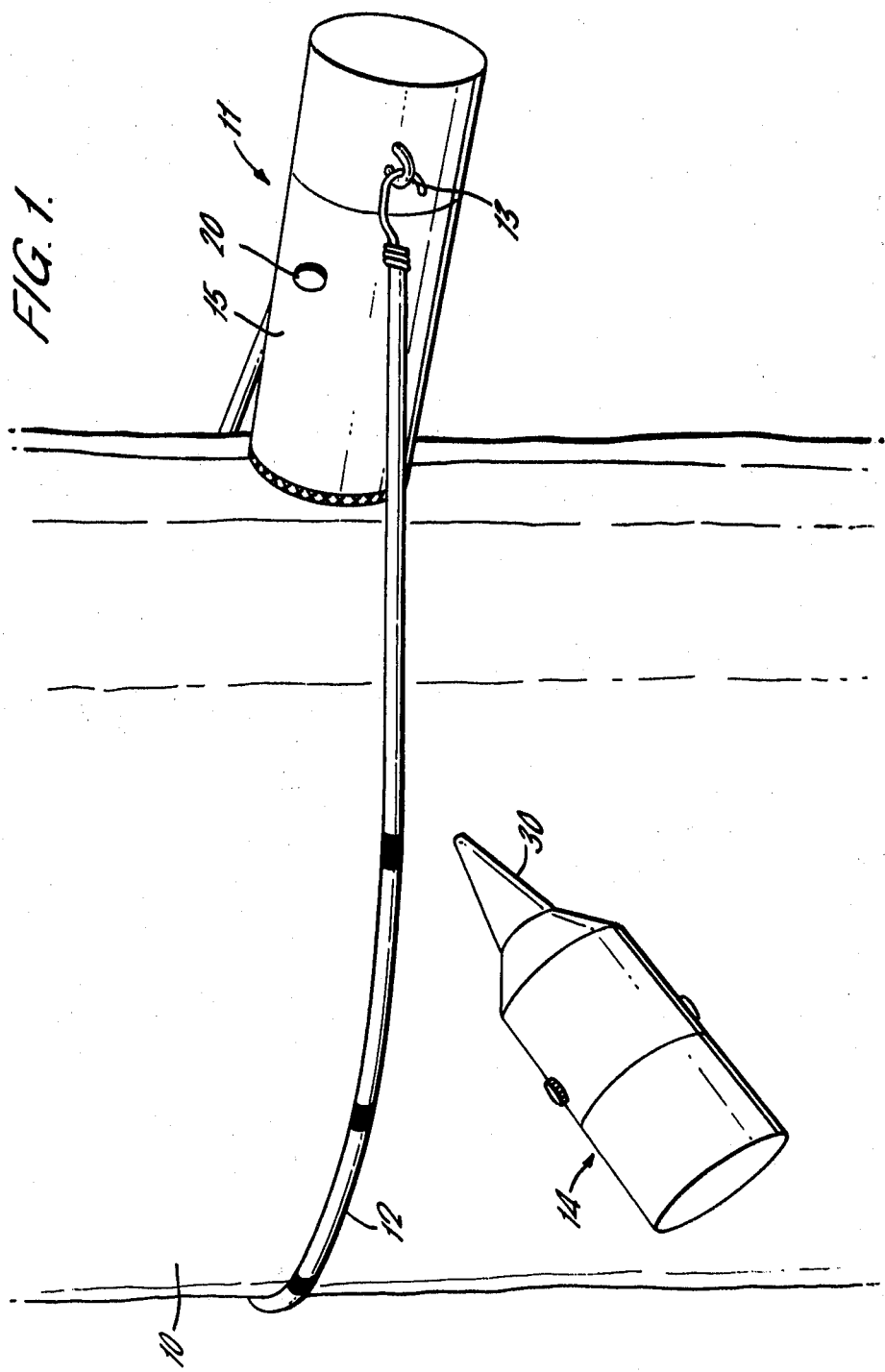

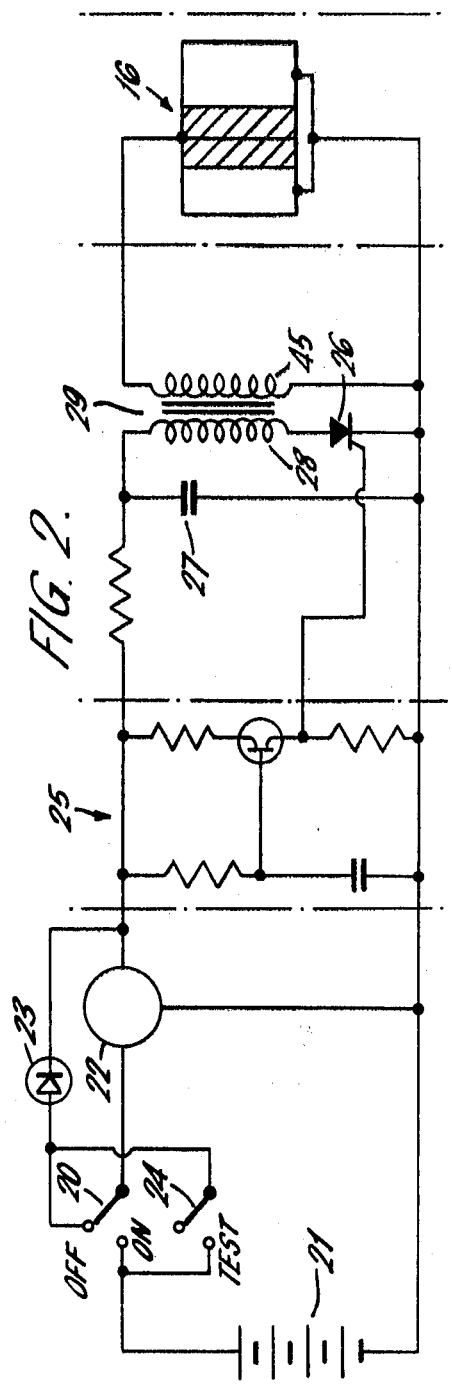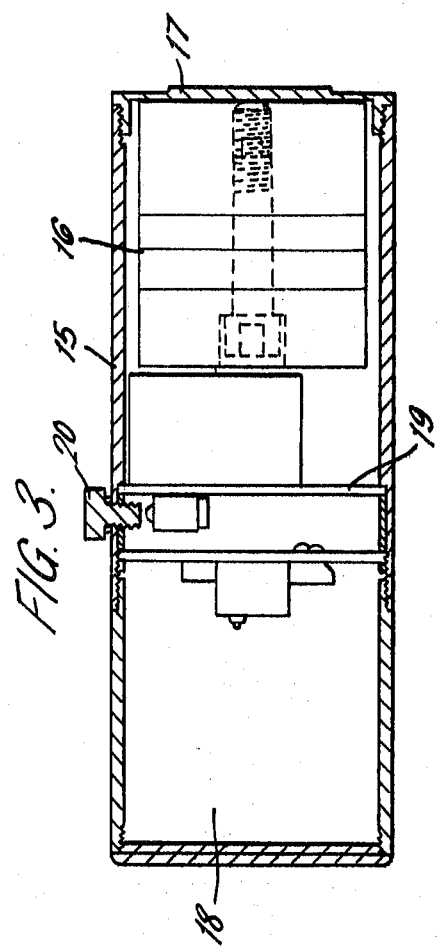

METHOD OF AND APPARATUS FOR TESTING WOODEN POLES

BACKGROUND OF THE INVENTION

1. Field of the Invention

This invention relates to a method of and apparatus for testing poles.

2. Prior Art

The usual method of testing wooden poles, such as are used for example for supporting electricity power distribution lines and telephone lines, is by sounding with a hammer and/or by taking borings. Various other techniques have been proposed in the past, for example using a piezo electric transducer to produce shock waves in the pole and measuring the transmission time through the pole. However difficulties have been experienced with such devices. Reference is made to U.S. Pat. Nos. 4,059,988; 3,877,294 and 3,531,983 as examples of such prior art.

BRIEF SUMMARY OF THE INVENTION

According to the present invention there is provided an apparatus for testing a wooden pole comprising a transmitter unit arranged to produce regularly repetitive pulses of ultrasonic energy for transmission into the pole transversely thereof when the transmitter unit is secured to a pole, the transmitter unit also producing audible signals synchronised with the ultrasonic pulses, and a separate receiver unit having a probe for placing against the surface of the pole, a receiver transducer for detecting ultrasonic signals picked up by the probe, and visual indicator means responsive to the transducer output to give a visual indication for each received pulse exceeding a predetermined amplitude. Preferably the receiver unit includes adjustable means for adjusting the level of amplitude required to effect operation of the indicator. The transducer unit and the receiver unit are conveniently battery powered.

It has been found that a patch of rot or decay in the pole between the transmitter and the receiver will cause significant attenuation of the ultrasonic signals transmitted through the wooden poles. The use of ultrasonic signals results in substantially straight line transmission from the transmitter and hence, by appropriate setting of the level at which the receiver responds, an indication will be obtained only if there is no rot on the line between the transmitter and the receiver.

The apparatus is used by fixing the transmitter at one point on the pole and then placing the receiver successively at a number of locations angularly spaced around the pole at the level of the transmitter. At each location it is observed whether or not the visual indicator on the receiver is operated in synchronism with the audible pulses from the transmitter, which pulses can be heard by the operator holding the receiver.

As will be explained in further detail later, by repeating such tests with the transmitter at two or more further locations at the same level but angularly displaced from the first position on the pole, it becomes possible to locate the regions of decay within the pole at that level. Furthermore, as will be explained, it becomes possible also to determine approximately the remaining strength of the pole.

The transmitter is conveniently a piezo electric transducer, e.g. a piezo electric sandwich transducer and it may typically be pulsed at a rate of about four times a second. The required audible signal may readily be obtained by appropriate construction of the transmitter and its housing so that there is an audible vibration of the housing each time the transmitter is pulsed.

The probe in the receiver conveniently is shaped to provide a small contact area with the wooden pole, the probe forming a matching unit for transmitting the received ultrasonic signal onto a much larger area of a piezo electric element constituting the receiver transducer.

The indicator means conveniently comprises a lamp which may be energised by or in synchronism with the output of a voltage comparator comparing the amplitude of the output of the receiver transducer with a preset reference signal from a reference signal source. Preferably means are provided for adjusting the level of the reference signal.

BRIEF DESCRIPTION OF THE DRAWINGS

FIG. 1 is a perspective diagram illustrating a transmitter unit attached to a wooden pole and showing also a receiver unit;

FIG. 2 is a circuit diagram of the transmitter unit;

FIG. 3 is a diagram, partly in sectional elevation, showing the construction of the transmitter unit;

DESCRIPTION OF THE PREFERRED EMBODIMENT

Figure 4:
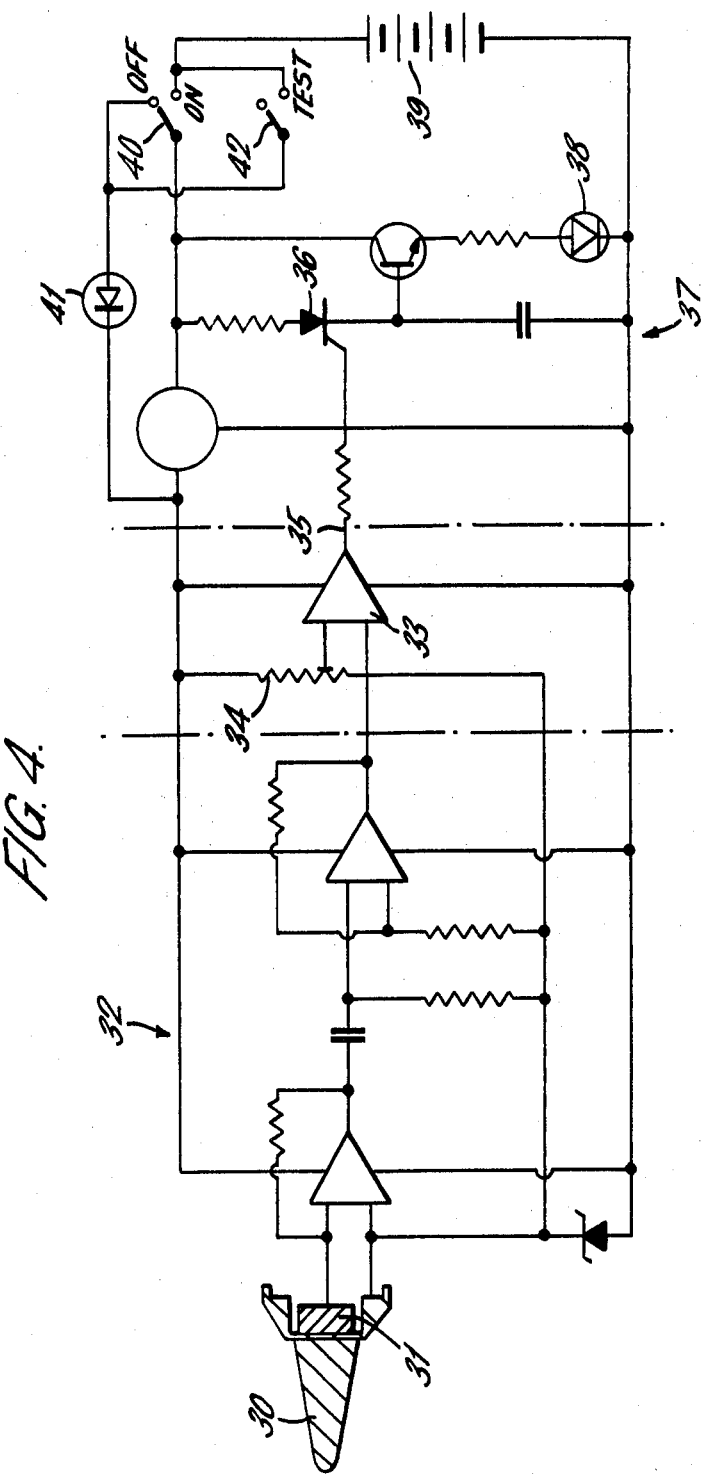
FIG. 4 is a circuit diagram of the receiver unit.

Referring to FIG. 1 there is shown a wooden pole 10 to be tested with a transmitter unit 11 secured onto the pole by means of an elastic flexible band 12 the ends of which are hooked in lugs 13, one on each side of the transmitter unit. There is a separate hand-held receiver unit 14 having a probe 30 for placing against the surface of the pole 10.

The transmitter unit 11 is shown in further detail in FIG. 3 and has a cylindrical housing 15 in one end of which is located a sandwich-type piezo electric transducer 16 using a piezo electric plate with aluminium and steel layers. This transducer lies closely against that end 17 of the housing which is placed in contact with the surface of the pole. The sandwich construction enables the transducer, when energised, to induce shock waves in the pole. Within the transmitter housing 15, there is a battery compartment 18 and printed circuit boards 19 carrying the required electronic components. An on-off switch 20 is mounted on the transmitter unit.

The transmitter circuit is shown in FIG. 2. A battery 21 is connected via switch 20 to a voltage regulator 22. A light-emitting diode constituting a battery test light 23 and switch 24 is provided, which is operable to indicate if the battery voltage is above the minimum operating voltage. A unijunction transistor pulsing circuit 25, energised by the regulated battery output, is connected to the gate of a thyristor 26 which conducts and discharges a capacitor 27 through a primary winding 28 of a transformer 29. A negative high voltage pulse from the transformer secondary winding 45 is applied to the piezo electric sandwich transducer 16. The thyristor 26 turns off when the capacitor 27 is discharged. This cycle is repeated four times a second, the repetitive rate being determined by the pulse circuit.

These repetitive pulses result in shock excitation of the transducer 16 which is resonant at an ultrasonic frequency thereby giving a short pulse of ultra-sound which is applied to the wooden pole when the transmitter is fixed in position. In this particular embodiment, the required audible sound, to be synchronised with each ultra-sound pulse, is produced by sub-harmonics of the ultrasonic vibration of the transducer and housing within the audible frequency range.

FIG. 4 illustrates diagrammatically the receiver unit 10 and shows the conical probe 30 which has a narrow end giving substantially point contact with the pole 10, when the receiver unit is held against the pole 10. This probe 30 forms a matching unit to a piezo electric transducer 31 which converts the ultra-sound signals picked up by the probe into an electrical output. This output is applied to a two-stage amplifier 32 and thence to a voltage comparator 33 where the amplitude of the signal is compared with an adjustable preset voltage reference signal from a reference signal unit containing an adjustable potentiometer 34 for setting the level of the voltage reference. The comparator 33 is arranged so that, if the amplitude of the input from the amplifier 32 exceeds that of the voltage reference, a pulse is produced on an output line 35. This pulse is fed to a thyristor 36 in a lamp control circuit 37 to cause a lamp 38 to flash at the pulse frequency.

Thus, if ultrasonic pulses are received through the pole 10 from the transmitter 11, then the lamp 38 will flash in synchronism with the ultrasonic pulse applied by the transmitter and hence in synchronism with the sound signals from the transmitter. The receiver is energised by a battery 39 and is made as a lightweight device which can be held in the hand and pressed against the pole. An on-off push button switch 40 is mounted on the receiver unit. A battery test lamp 41 and switch 42 is provided. When the switch 42 is closed, the lamp 41 lights, only if the battery voltage is above the required operating voltage for the receiver circuit.

In practice the level at which the voltage reference signal has to be set on potentiometer 34 is independent of the thickness of the pole over a relatively wide range. It is readily possible to set a suitable level by empirical testing, or by calibration, so that the instrument can be used to detect rot in poles. If there is rot between the transmitter and receiver, no signal will be detected whereas if the whole of the direct path between the transmitter and receiver is through good wood, then the lamp 38 will flash in synchronism with the sound signals.

Figure 5A:
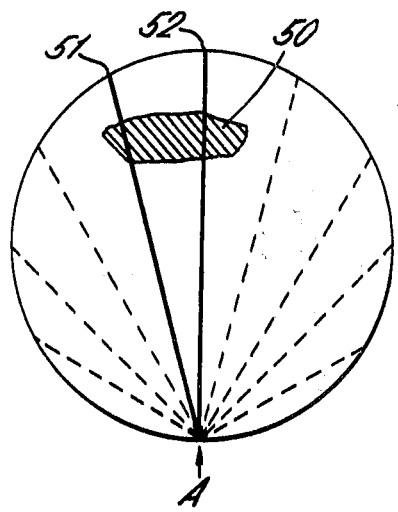
FIGS. 5a, b, c and d are diagrammatic cross-sections through a pole showing the transmitter and receiver at various locations for explaining how a region of decay is located.
Figure 5B:
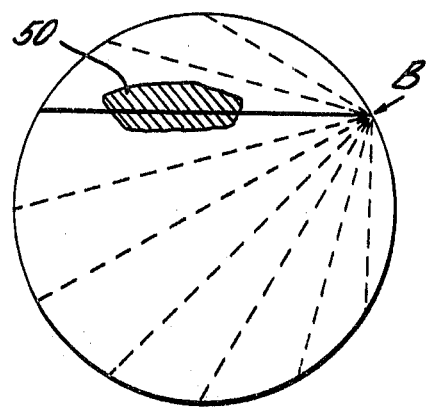
Figure 5C:
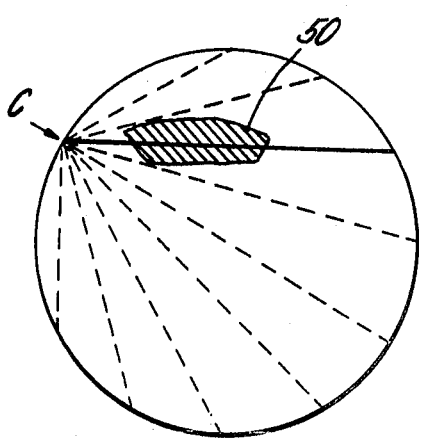
Figure 5D:
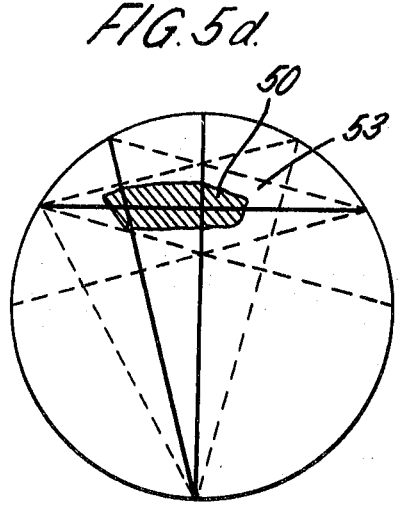

To use this device, typically the transmitter is attached to the wooden pole at a suitable height, for example 2 feet above ground level, and the pole is tested by placing the receiver at various points against the pole at and above and below this height. If no rot is found, then the transmitter is moved to another point for example 6 feet above ground level and the test is then repeated. If at any point rot is detected, then the location of the rot is determined in the following manner. The transmitter is strapped onto the face of the pole at the height where rot has been detected. For poles carrying power lines where strength in a particular plane is required, the transmitter is preferably located on the neutral axis. The receiver is applied to the wooden pole at a point opposite to the transmitter and is also applied to the pole at four points spaced 30° around the pole on each side of that position. The receiver is thus put in nine different positions around the pole, all at the same height as the transmitter. For convenience the fixing rope 2 holding the transmitter onto the pole may be marked to indicate the required points. This test is then repeated with the transmitter at the same height but at two different angular positions which are 120° on either side of the original position on the circumference of the pole. A total of twentyseven readings are thus recorded, each reading indicating whether or not a signal is received. The lines of the various direct transmitter to receiver signal paths for these various tests form a grid throughout the pole at that section. Referring to FIG. 5, in 5a there is shown an area of rot 50. The transmitter is put at point A and the straight lines radiating from point A indicate the various positions at which the receiver is located. Typically nine such positions will be employed as explained above. It will be seen that at positions 51 and 52, the direct lines from the transmitter pass through the area of rot and hence no signal will be received. At the other positions a signal will be received. The test is then repeated with the transmitter at B as shown in FIG. 5b and it is seen that there is one receiver position at which the rot will be detected. The third test is carried out with the transmitter at position C as shown in FIG. 5c and again there is one position where the rot has been detected. FIG. 5d shows how these results, when combined, indicate that the rot lies within the shaded area shown at 53.

For a pole carrying power lines, it may be desired to determine how much strength remains in the pole to resist the bending forces which are transverse to the direction of the line. This strength may be determined, conveniently using a computer, from the 27 good or bad readings. One convenient way of making this computation is consider the cross-section of the pole to be divided into a large number of equal-sized small squares, typically 1264 squares. Each square is assessed by its proximity to the scan lines through the pole and, if the square is close to a "good" line, it is considered to be of good wood. The "good" squares are used to calculate the moment of inertia of the pole about the required axis. The ratio of this calculated moment of inertia to that of a completely sound pole indicates the percentage of the original pole strength that remains effective.

We claim:

1. Apparatus for testing a wooden pole comprising a transmitter unit arranged to produce regularly repetitive pulses of ultrasonic energy for transmission into the pole transversely thereof when the transmitter unit is secured to a pole, the transmitter unit also producing audible signals synchronised with the ultrasonic pulses, and a separate receiver unit having a probe for placing against the surface of the pole, a receiver transducer for detecting ultrasonic signals picked up by the probe, and visual indicator means responsive to the transducer output to give a visual indication for each received pulse exceeding a predetermined amplitude.

2. Apparatus as claimed in claim 1 wherein the transmitter unit includes a battery power supply.

3. Apparatus as claimed in claim 1 wherein the receiver unit includes a battery power supply.

4. Apparatus as claimed in claim 1 wherein the receiver unit includes adjustable means for adjusting the level of amplitude required to effect operation of the indicator.

5. Apparatus as claimed in claim 1 wherein the transmitter comprises a piezo electric transducer.

6. Apparatus as claimed in claim 5 wherein the transducer in the transmitter is located in a transmitter housing and wherein the transmitter and its housing are constructed so that there is an audible vibration of the housing each time the transducer is pulsed so as thereby to produce an audible sound.

7. Apparatus as claimed in claim 1 wherein the transmitter comprises a piezo electric sandwich transducer.

8. Apparatus as claimed in claim 1 and having an elastic flexible band adapted to be secured to the transmitter for stretching around a pole to hold the transmitter on the pole.

9. Apparatus as claimed in claim 1 wherein the probe in the receiver unit is shaped to provide a small contact area with the wooden pole, the probe forming a matching unit for transmitting the received ultrasonic signal onto a much larger area of a piezo electric element constituting said receiver transducer.

10. Apparatus as claimed in claim 1 wherein the indicator means conveniently comprises a lamp energised by or in synchronism with the output of a voltage comparator comparing the amplitude of the output of the receiver transducer with a preset reference signal from a reference signal source.

11. Apparatus as claimed in claim 10 wherein means are provided for adjusting the level of the reference signal from the reference signal source.

12. A method of testing a wooden pole using the apparatus as claimed in claim 1 wherein the transmitter is secured to the pole to apply ultrasonic vibrations to the pole and wherein the receiver probe is put in contact with the pole at a plurality of separate positions, observation being made as to whether or not, in each position, the visual indicator is energised in synchronism with the audible signals.

13. A method as claimed in claim 12 wherein the observations are made with the receiver in a plurality of predetermined locations with respect to the transmitter for each of a plurality of transmitter positions whereby the presence or absence of rot in each of a number of predetermined regions of the cross-section of the pole can be determined, and computing the remaining strength in the pole corresponding to the sound regions.

* * * * *